United States Patent [19]

Ault

[11] Patent Number: 5,804,172
[45] Date of Patent: Sep. 8, 1998

[54] COMPOSITIONS AND METHODS FOR REMOVING MINERALS FROM HAIR

[75] Inventor: Frederick K. Ault, Muncie, Ind.

[73] Assignee: Vitachlor Corporation, Muncie, Ind.

[21] Appl. No.: 705,545

[22] Filed: Aug. 29, 1996

Related U.S. Application Data

[63] Continuation of Ser. No. 387,608, Feb. 13, 1995, abandoned, which is a continuation of Ser. No. 41,530, Apr. 1, 1993, abandoned, which is a continuation of Ser. No. 807,086, Dec. 13, 1991, abandoned.

[51] Int. Cl.⁶ .............................. A61K 7/00; A61K 7/06
[52] U.S. Cl. ........................................... 424/70.1; 424/401
[58] Field of Search .................................... 424/70.1, 401

[56] References Cited

U.S. PATENT DOCUMENTS 4,581,229  4/1986  Petrow ...................................... 424/70
4,690,818  9/1987  Puchalski .................................. 424/70

*Primary Examiner*—Sally Gardner Lane
*Attorney, Agent, or Firm*—Woodard, Emhardt, Naughton Moriarty & McNett

[57] ABSTRACT

A composition for use in removal of minerals from hair is disclosed herein which comprises the combination of an acidifying agent, a reducing agent, a chelating agent, a gelling agent and water. A synergistic combination of chelating agents is disclosed. Also disclosed herein is a process for packaging the inventive compositions, and a method for removal of mineral residues from hair by use of compositions as disclosed.

6 Claims, No Drawings

COMPOSITIONS AND METHODS FOR REMOVING MINERALS FROM HAIR

This application is a continuation of application Ser. No. 08/387608, filed, Feb. 13, 1995 now abandoned, which is a continuation of Ser. No. 08/041,530 filed Apr. 1, 1993, now abandoned which is a continuation of U.S. Ser. No. 07/807,096 filed Dec. 13, 1991 now abandoned.

BACKGROUND

The present invention relates to the field of hair treatment and particularly to mineral removal from the hair shaft.

Despite the widespread need for a simple and effective treatment to remove minerals from the hair, prior art methods have been ineffective in removal of these mineral deposits from the hair shaft. More than 50 percent of the American people use well water which can lead to mineral deposits on hair and scalp. Many communities have municipally supplied "hard" water which may lead to mineral deposits on hair. Mineral deposits may discolor the hair shaft and also alter the texture of hair to make hair brittle. Minerals must also be removed prior to application of permanent hair treatments. Minerals in hair may also lead to unwanted hair color when hair is bleached or color is applied. Common minerals in water that form deposits on hair include calcium, magnesium, iron and copper, along with small amounts of lead, chromium, tin and zinc. These minerals are metals that carry a positive electrical charge and may be found in their higher oxidation states. These metals in their higher oxidation states may act as oxidizing agents.

Common mineral residues such as iron, copper and lead produce obvious discoloration of hair, in which iron is reddish orange, copper is green and lead is black. Calcium and magnesium are not colored, but manifest their presence by giving the hair a dry, brittle feel. These minerals form deposits that can not be removed from the hair and skin through normal processes and techniques.

Hair and skin are composed mainly of protein. The protein in hair is arranged in such a way that the tertiary protein structure carries a weak negative electrical charge which may attract minerals that have a positive charge. The protein in hair is composed in part of a sulphur-containing amino acid called cysteine. Two cysteine molecules can bond together through oxidation to form cystine, which has a covalent disulfide bond that is quite strong. The mineral deposits in the water which contain a positive charge are attracted to the negative charge on the hair strand and may oxidize the free cysteine by acting as oxidizing agents. These oxidizing agents may also form covalent bonds with the cysteine residue.

Heretofore, these mineral protein interactions were considered to be mostly ionic and mechanical, due to the attractions between the positive charge on the mineral and the negative charge on the hair. This belief led previous attempts to remove mineral build-up to focus on the use of alkaline chelating solutions containing one or more derivatives of ethylene diamine tetraacetic acid (EDTA). These previous attempts to reduce mineral build-up on hair have only had marginal efficiency due to their focus on the ionic component of this problem.

It is important for minerals in the hair to be removed prior to a permanent because the minerals interfere with the chemical reactions in the permanent wave systems utilized to relax the hair shaft. Salts of thioglycolic acid are used as reducing agents in permanent wave systems. These salts are generally ammonium, calcium or sodium derivatives of thioglycolic acid. Thioglycolate, when applied to hair, breaks disulfide bonds, which thereby relaxes or straightens the hair and allows the protein structure to be rearranged into a different conformation through the process and treatment. If thioglycolate is added to hair containing iron, iron binds to the thioglycolate ion and produces an intense reddish purple color. Typically, iron laden hair will literally drip purple solution off the hair when a permanent wave solution is applied. This effect of turning the hair purple is undeniably an undesirable effect. Minerals that are covalently bound to the hair strands also interfere with the ability of the thioglycolic acid to interact with the hair strand to relax, straighten, or provide a new set for the hair through the process and treatment.

SUMMARY OF THE INVENTION

One aspect of the present invention relates to a composition suitable for removing minerals from hair comprising an acidifying agent, a reducing agent, at least one chelating agent and a gelling agent. This composition reduces oxidized minerals in a weakly acidic environment, thereby preparing the minerals for the chelating agent to sequester and remove the minerals from the hair strand. Another aspect of the present invention involves the process of packaging a weakly acidic composition suitable for removing minerals from hair in an air-tight package in an oxygen-free environment. This process of packaging is necessary to maintain the effectiveness of the composition.

It is an object of the present invention to provide a weakly acidic composition suitable for removing minerals from hair which includes an acidifying agent, a reducing agent, at least one chelating agent and a gelling agent.

It is another object of the present invention to provide a process of packaging a weakly acidic composition suitable for removing minerals from hair which includes providing an acidifying agent, a reducing agent, at least one chelating agent and a gelling agent and packaging said agents in an air-tight package in an oxygen-free environment to pressure the effectiveness of such agents.

A further object of the present invention is to provide a process for removing minerals from hair shafts which may reduce hair discoloration, improve texture and also increase the effectiveness of permanents and other hair treatments.

Further objects and advantages of the present invention will become apparent from the description of the preferred embodiment which follows.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such alterations and further modifications in the device, and such further applications of the principles of the invention, being contemplated as would normally occur to one skilled in the art to which the invention relates.

Hair is comprised of hair shafts which are further comprised of protein that may bind minerals by both ionic bonds and covalent bonds as will be more fully described. The present invention in various embodiments provides compositions and processes for removing the minerals from hair shafts.

The inventive compositions include four ingredients, an acidifying agent, a reducing agent, a chelating agent and a gelling agent. The compositions are able to reduce metallic minerals and sequester these minerals from the hair protein by use of chelating agents. The weakly acidic environment aids in removal of the minerals by reducing the bond strength of the minerals to the hair protein. The reducing agent also functions to weaken the cysteine-metal bond strength and increase the efficiency of the chelating agents. The chelating agent removes metals from the hair shaft after the acidifying agent and reducing agent have weakened the bond that retains them. The invention is formulated as a gel to retain the composition in intimate contact with the hair shaft. The inventive compositions are preferably applied in combination with heating of the compositions and/or hair, as the heat expands the hair shafts to provide entry of the composition into the hair shaft and increase the reaction rate.

Several of the ingredients of the composition may serve more then one function. Ascorbic acid serves as both an acidifying agent and reducing agent. EDTA, citric acid, and gluconic acid are chelating agents that also serve as acidifying agents due to their weakly acidic nature.

Weak acids and their salts are utilized in the inventive composition to provide an acidic environment that is safe for use on the hair shafts and which weakens the bond strength of the cysteine-metal bond. This weakening of the bond allows the chelating agent to perform more efficiently in removing the minerals from the hair shaft by reduction of the bond strengths. Although a specific pH is not critical to the operation of this invention, it is advantageous to provide a pH in the range of 2 to 5, preferably about 2.5.

A reducing agent is included in the inventive composition to transfer electrons to the oxidized iron, copper, lead, chromium and tin and other oxidized metals to reduce their oxidation state and thereby lower the strength of the cysteine-metal bond. For example, the reduction of iron from $Fe^{3+}$ to $Fe^{2+}$ reduces the strength of the cysteine-iron bond thereby increasing the ease of sequestration of the iron by the chelating agent. The reducing agent must be carefully chosen so that it has sufficient strength to provide effective reduction of the oxidized cysteine-iron bond and is gentle to hair so that the structure of the hair shaft is not injured. The electrode potential of the reducing agent is selected so that it is below that of the metal ions but above the potential of the cysteine bond, otherwise the structure of the hair will be destroyed upon treatment. Ascorbic acid is a sufficiently strong reducing agent to allow the chelating agent to remove the unwanted minerals from the hair shaft and is also safe for use on hair. Ascorbate or ascorbic acid is a preferred reducing agent and its minimum effective strength is about 2.1 percent, although a higher concentration may be used.

Once the ascorbic acid has come in contact with the cysteine metal complex and the metal is reduced, a strong chelating agent in an effective concentration must be available to attach to the reduced metal ions. To be effective, the bond energy between the reduced metal ion and the chelating agent must be stronger than the mostly covalent bond between the metal ion and the cysteine ion or the bond energy of the metal ion cysteine bond must be further reduced. The weakly acidic nature of the inventive compositions, in combination with the reducing agent reduces the metal cysteine bond strength to the point that the mixture of chelators or chelator may be used effectively. A chelating agent mixture of disodium EDTA, sodium or potassium gluconate and citric acid with sodium or potassium citrate or various combinations thereof may be utilized to provide a chelating matrix. A mixture of chelating agents provides a more effective metal chelation to help remove the metals from the cysteine residues located in the tertiary protein structure of the hair strand. A mixture of 1.5 percent disodium EDTA, 2.7 percent sodium gluconate, 0.42 percent citric acid and 0.42 percent sodium citrate (w/w) in water in these proportions provides an intense synergistic chelating environment that maximizes chelating agent ion to cysteine-metal ion contact and is a sufficient quantity of chelating agent to remove minerals from hair. The proportion of chelating agents in the synergistic mixture, in dry form, is approximately 30 percent disodium EDTA, 55 percent sodium gluconate, 8 percent citric acid and 8 percent sodium citrate (w/w).

A gelling agent is included in the inventive composition to retain the composition in intimate contact with the hair shaft. The gelatinous consistency of the inventive composition is necessary to retain the composition on the hair shaft and allows the hair stylist to force the compositions into the hair shaft by squeezing with application of firm pressure.

Various combinations of the four ingredients may be formulated, depending on intended use. Ingredients simply need be compatible and efficacious with one another, and present in amounts suitable to perform the functions indicated. An especially preferred embodiment of the invention includes 2.1 percent w/w ascorbic acid which is utilized as a reducing agent and an acidifier, disodium EDTA 1.5 percent, sodium gluconate 2.7 percent, citric acid 0.42 percent and sodium citrate 0.42 percent w/w in water to produce a synergistic chelating environment, and 1 percent w/w xanthan gum which provides a medium for holding the composition onto the hair shaft thereby enabling the stylist or user to squeeze the acidic gel into the warm expanded hair shaft. The especially preferred embodiment of the invention in dry form is about 26 percent ascorbic acid, 18 percent disodium EDTA, 33 percent sodium gluconate, 5 percent citric acid and 5 percent sodium citrate and 12 percent w/w xanthan gum.

The invention may be packaged or as a dry powder to which the user adds water or as a ready to use gel for convenient application. A preferred process for packaging the invention includes packaging the acidifying agent, reducing agent, chelating agent and gelling agent in an air-tight package in an oxygen-free environment. The oxygen-free environment may be achieved through use of nitrogen gas in the packaging procedure. To package the invention as a gel, the acidifying agent, reducing agent, chelating agent and gelling agent are combined with water in an oxygen-free environment. The resulting weakly acidic gel is packed in an air-tight, oxygen-free package. The invention may be packaged under nitrogen to reduce oxidation. Actual mixing and packaging steps may be performed in accordance with conventional methods for handling materials in an oxygen-free environment. It is important that the invention be stored in an air-tight container since exposure to the atmosphere may allow the reducing agent to become oxidized and thereby negate its usefulness as such.

EXAMPLE 1

HAIR STRAND TEST

Initial tests of this invention were performed on six people. These and other tests have demonstrated that after 45 minutes iron is removed from the hair strands. This testing procedure may be useful at different timing intervals to determine the length of time needed for the invention to remain in contact with the hair shaft to remove the minerals for initial use of the inventive process. A stylist is able to gauge the correct amount of exposure time for the inventive compositions after a brief experience with the invention.

A powder mixture was prepared that included sufficient amounts of each of the following components to yield 2.1 percent w/w ascorbic acid, 1 percent w/w xanthan, 1.5 percent w/w disodium EDTA, 2.7 percent w/w sodium gluconate, 0.42 percent w/w sodium citrate and 0.42 percent w/w citric acid when added to 60 g. of water. Two hair samples were taken for iron tests; one was used as a control, and one was treated with the inventive composition. The control was tested with thioglycolate, which is used for permanents, to demonstrate tie presence of iron. The test sample was treated with the inventive composition for 45 minutes. The control sample was utilized to determine whether any iron was present in the hair. If iron is present, a intense reddish purple color will become evident. If no color develops, the hair may not be in need of treatment.

In order to prepare the test sample, the water was added to the dried powder, mixed throughly and allowed to stand for two minutes to allow the xanthan to hydrate. The mixture was placed on the hair strand and aggressively massaged into the hair strand for approximately 1 minute. The Rand was then placed in a 45° C. environment for 45 minutes. After 45 minutes, the hair strand was rinsed with water and a mixture of shampoo and water. After the hair strand was rinsed, thioglycolate was applied to the hair strand, and the hair strand was observed to determine whether a reddish purple color was present to indicate the presence of iron. The inventive composition and process was able to remove the iron after 45 minutes as evidenced lack of purple color production.

The inventive process is utilized by washing the hair with shampoo and rinsing with warn water to open the hair cuticles, applying the inventive compositions and throughly working the gel into all hair and scalp utilizing massaging action and pressure of palms and fingertips. The inventive process also removes mineral deposits from the scalp. After the gel is massaged into the scalp and hair shafts, the gel is retained on the hair shafts and kept at an elevated temperature of approximately 45° C. The temperature may be maintained by use of a heat cap or hair dryer. The hair is also periodically massaged and the gel worked into the hair shafts to assure an even distribution of heat and the composition throughout the hair to aid in mineral removal. The inventive composition is recommended to be applied to the hair shafts for 10 minutes if a light mineral build-up is encountered, and up to 45 minutes for a heavy mineral build-up. After the appropriate time has elapsed, the composition is rinsed off with water and a mixture of water and detergent. It is also possible to repeat the the inventive process as it does not produce drying or harmful effects to the hair shafts.

Because minerals often become deeply embedded into the hair shafts, the inventive process requires the application of heat. The shafts are preferably expanded by heat to open the cuticles and to make the hair more porous to allow the inventive composition to reach the cysteine-mineral residues. The inventive process includes using relatively hot water to shampoo the hair, which expands the hair shafts, opens the cuticles and also increases the reaction rate. When the hair cuticles are open, the inventive compositions are applied.

While the invention has been described in detail in the foregoing description, the same is to be considered as illustrative and not restrictive in character, it being understood that only the preferred embodiment has been described, and that all changes and modifications that come within the spirit of the invention are desired to be protected.

What is claimed is:

1. An acidic aqueous composition suitable for removing iron from hair comprising:
   (a) an acidifying agent effective to provide an acidic environment of pH between about 2 and about 5 when the composition is used in solution on hair;
   (b) an ascorbic acid reducing agent present at a concentration of at least 2.1 percent w/w effective to reduce the oxidation state of iron ions bonded to hair from the $Fe^{3+}$ oxidation state to the $Fe^{2+}$ oxidation state;
   (c) a chelating agent effective to remove iron ions covalently bonded to hair, said chelating agent comprising 1.5 percent disodium EDTA, 2.7 percent sodium gluconate, 0.42 percent citric acid and 0.42 percent sodium citrate (w/w) of composition;
   (d) a gelling agent; and
   (e) water.

2. The composition of claim 1 wherein the ascorbic acid reducing agent is present at a concentration of 2.1 percent w/w of composition and the gelling agent is xanthan gum at a concentration of about 1 percent w/w of composition.

3. A process for removing minerals from hair shafts comprising the steps of:
   (a) providing a gel including:
      (i) an acidifying agent effective to provide an acidic environment of pH between about 2 and about 5 when the gel is used in solution on hair;
      (ii) an ascorbic acid reducing agent present at a concentration of at least about 2.1 percent w/w effective to reduce the oxidation state of iron ions bonded to hair;
      (iii) a chelating agent effective to remove iron ions covalently bonded to hair, said chelating agent comprising 1.5 percent disodium EDTA, 2.7 percent sodium gluconate, 0.42 percent citric acid, and 0.42 percent sodium citrate w/w of said gel;
      (iv) a gelling agent; and
      (v) water;
   (b) contacting said gel with the hair shafts at an elevated temperature;
   (c) forcing and massaging said gel into said hair shafts;
   (d) leaving said gel on said hair shafts at a temperature of about 45° C. a sufficient time to remove iron from said hair shafts; and
   (e) rinsing said gel from said hair shafts with water.

4. The process of claim 3 in which the chelating agent consists essentially of 30 percent disodium EDTA, 55 percent sodium gluconate, 8 percent citric acid and 8 percent sodium citrate (w/w).

5. The process of claim 3 in which the gel comprises 2.1 percent ascorbic acid and the gelling agent is xanthan gum at a concentration of 1 percent w/w of said gel.

6. The process of claim 5 in which the gel consists essentially of 2.1 percent ascorbic acid, 1.5 percent disodium EDTA, 2.7 percent sodium gluconate, 0.42 percent citric acid, 0.42 percent sodium citrate and 1 percent w/w xanthan gum w/w of the gel.

* * * * *

UNITED STATES PATENT AND TRADEMARK OFFICE
CERTIFICATE OF CORRECTION

PATENT NO. : 5,804,172
DATED : September 8, 1998
INVENTOR(S) : Frederick K. Ault It is certified that error appears in the above-indentified patent and that said Letters Patent is hereby corrected as shown below:

At column 1, line 8, "096" should read --086--.

At column 2, line 38, "pressure" should read --preserve--.

At column 5, line 22, "Rand" should read --hair strand--.

At column 5, line 33, "warn" should read --warm--.

Signed and Sealed this

Sixteenth Day of November, 1999

Attest:

Q. TODD DICKINSON

*Attesting Officer*  *Acting Commissioner of Patents and Trademarks*